United States Patent [19]
Lemke et al.

[11] Patent Number: 6,080,138
[45] Date of Patent: Jun. 27, 2000

[54] IV PROTECTOR

[76] Inventors: Christy L. Lemke, 13534 W. Park Dr., Magalia, Calif. 95954; Jean M. DeLapp, 2368 Stearns Rd., Paradise, Calif. 95969

[21] Appl. No.: 09/159,237

[22] Filed: Sep. 23, 1998

[51] Int. Cl.[7] ............................. A61M 5/00; A61M 5/32
[52] U.S. Cl. ..................... 604/263; 604/163; 604/198; 128/919
[58] Field of Search ............................. 604/110, 162–63, 604/171, 192, 198, 263; 128/917–18, 919

[56] References Cited

U.S. PATENT DOCUMENTS

| | | | |
|---|---|---|---|
| 4,551,137 | 11/1985 | Osborne | 604/171 |
| 4,943,283 | 7/1990 | Hogan | 604/198 |
| 4,943,284 | 7/1990 | Ehrlich . | |
| 5,011,475 | 4/1991 | Olson . | |
| 5,112,313 | 5/1992 | Sallee . | |
| 5,116,324 | 5/1992 | Brierly et al. . | |
| 5,267,972 | 12/1993 | Anderson . | |
| 5,343,875 | 9/1994 | Chase . | |
| 5,344,404 | 9/1994 | Benson . | |
| 5,366,447 | 11/1994 | Gurley . | |
| 5,603,699 | 2/1997 | Shine . | |
| 5,685,860 | 11/1997 | Chang et al. . | |
| 5,749,860 | 5/1998 | Kyte | 604/192 |
| 5,851,196 | 12/1998 | Arnett | 604/110 |

FOREIGN PATENT DOCUMENTS

WO97/21458  6/1997  WIPO ..................... 604/263

*Primary Examiner*—Mark O. Polutta
*Assistant Examiner*—Patricia M. Bianco
*Attorney, Agent, or Firm*—Richard C. Litman

[57] ABSTRACT

The IV protector of the present invention is a device designed to prevent spattering of blood from the tip of a peripheral IV catheter during removal and disposal of the catheter and IV tubing. The IV protector is a flexible plastic cylinder about three inches in length and about 1.5 cm in diameter. At one end it has a projection and a mating groove clasp fastener in order to seal the end of the cylinder by pinching the projection into the groove. At the other end the cylinder has internal threads adapted to lock the IV protector in a retracted position circumferentially about the IV tubing when the catheter is inserted in the venipuncture site, and adapted to lock the IV protector in an extended position circumferentially enclosing the catheter for disposal. A pair of resilient threaded washer shaped adaptors which snap fit on the IV tubing, or tubular adaptors having a hub adapted for connection to the catheter hub at one end and adapted for connection to the needle adaptor of the IV tubing at the other end are used to dispose the IV protector between the IV tubing and the catheter.

5 Claims, 5 Drawing Sheets

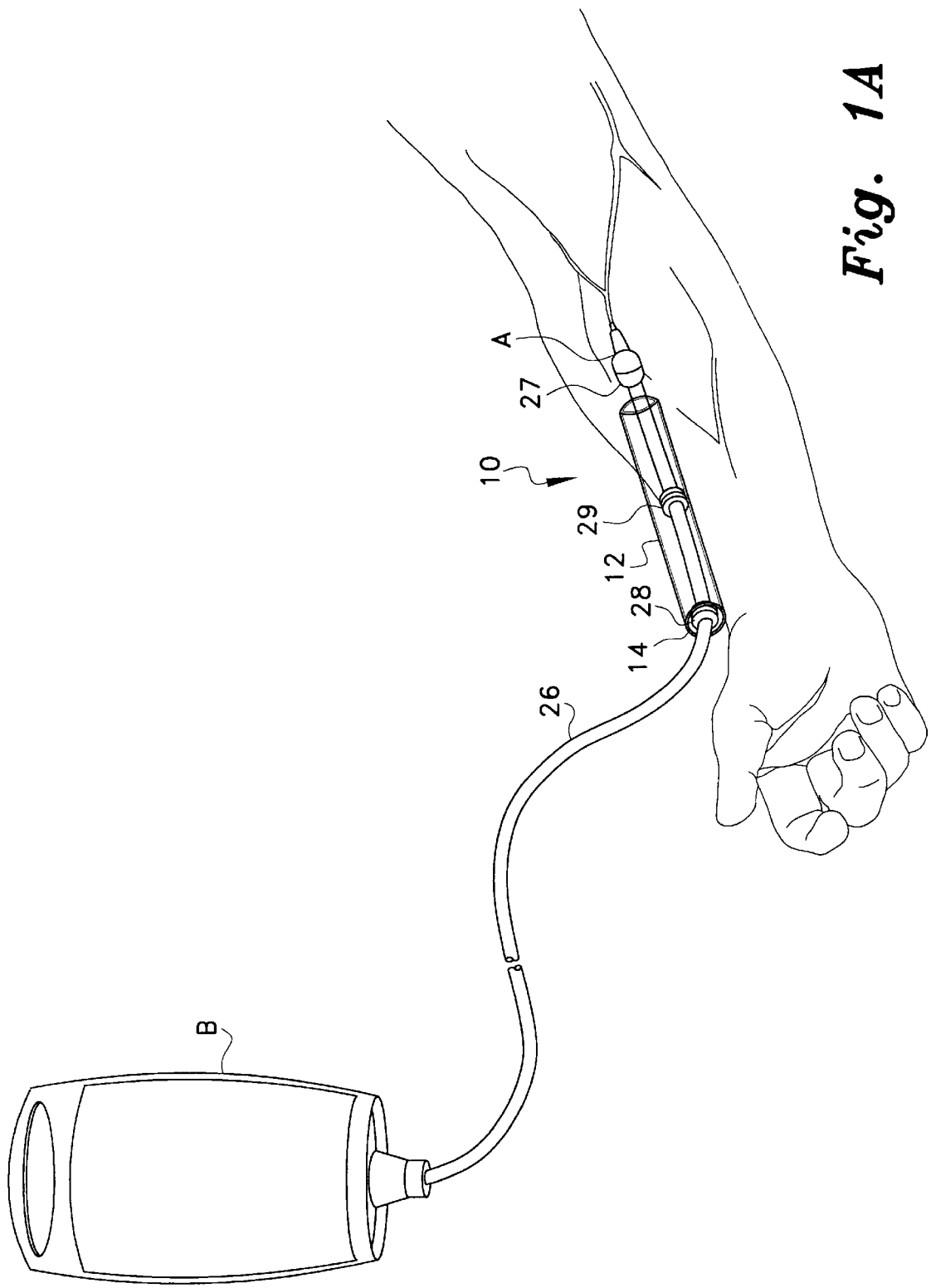

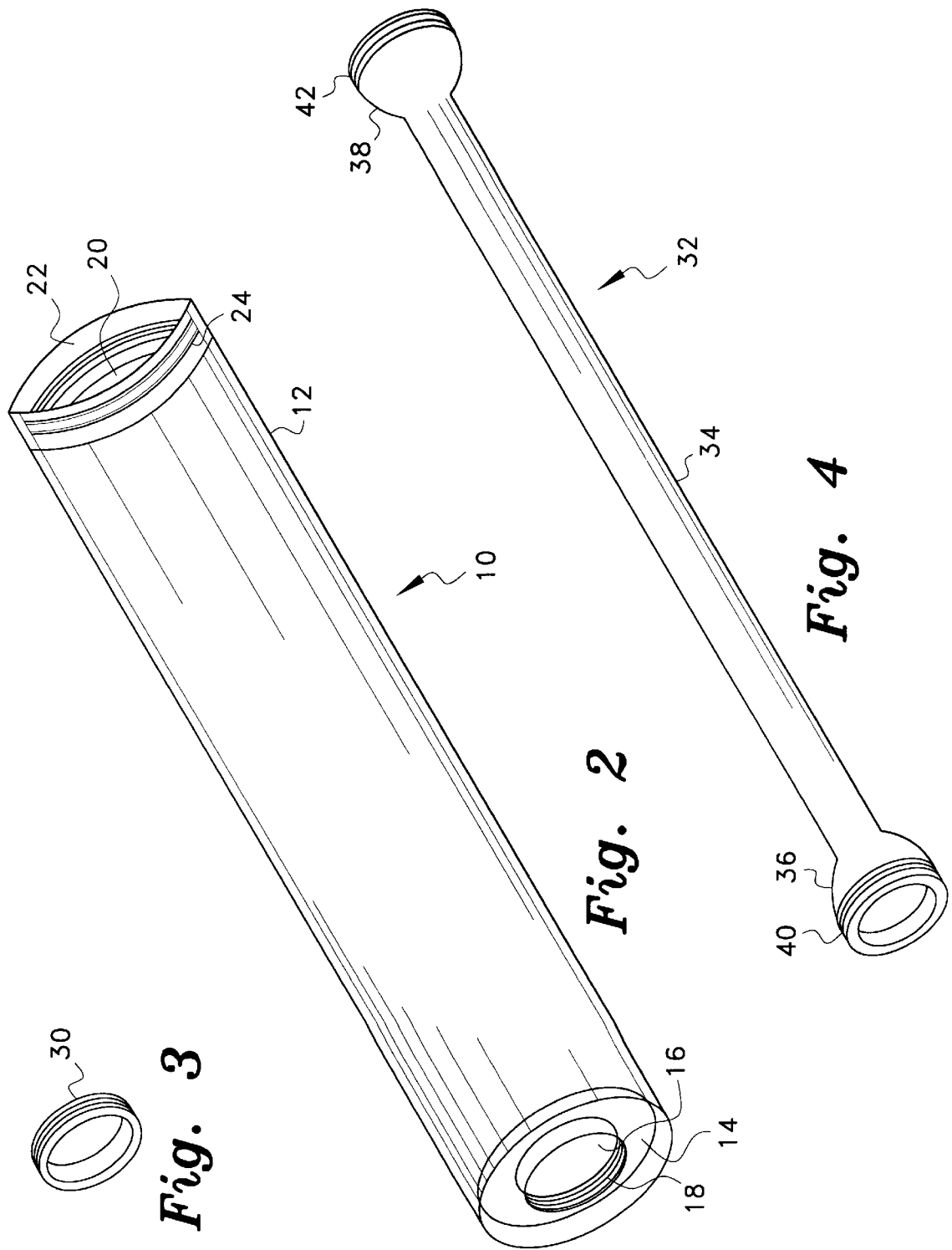

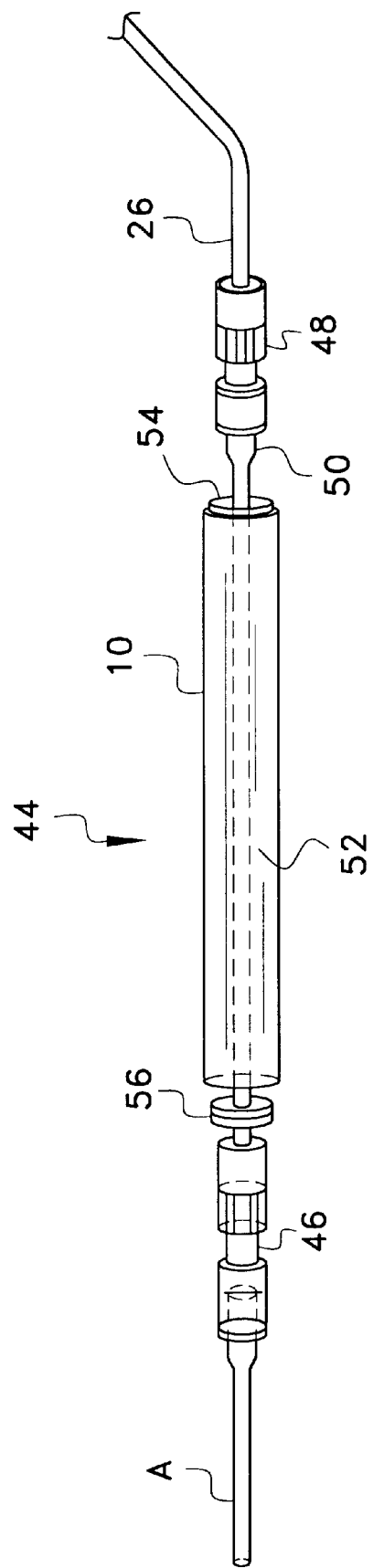

IV PROTECTOR

BACKGROUND OF THE INVENTION

1. Field of the Invention

The present invention relates to medical and surgical protective devices and shields, and particularly to an IV protector which encloses an IV catheter attached to IV tubing in a protective sheath to avoid contamination and the risk of spreading infection encountered from the spattering of blood which normally occurs when removing and disposing of the catheter and the tubing.

2. Description of the Related Art

Intravenous (IV) therapy is a versatile technique used for the administration of fluids. It has been used for such purposes as the maintenance of fluid and electrolyte balance, the transfusion of blood, administration of nutritional supplements, chemotherapy, and the administration of drugs and medications. Fluids may be administered intravenously by injection through a hypodermic syringe, or intermittently or continuously by infusion using a needle or a plastic or silicon catheter.

Although there are many advantages to be derived from the intravenous administration of fluids, the past two decades have brought heightened awareness of the risks of propagating infectious diseases associated with the technique, particularly due to the HIV virus. One consequence of this heightened awareness has been the development of various devices to reduce the risk of spreading infectious diseases. Probably the majority of devices which have been developed are concerned with the danger of accidental puncture wounds occurring through use of the hypodermic syringe needle or to the particular needle or trocar used to introduce a continuous infusion IV catheter.

Continuous infusion IV therapy may be generally divided between peripheral IV therapy and central venous IV therapy, depending on the site of administration. Catheters used for peripheral IV therapy tend to be short, between ¾" and 1 ¼" long, or occasionally 2" long for insertion into a deep vein. Catheters for central venous IV therapy tend to be much longer, and are outside the scope of the present invention.

A peripheral IV catheter is made of soft, flexible plastic or silicon, generally between 16 gauge and 24 gauge. In a procedure known as venipuncture the catheter is inserted into a vein in the patient's hand, foot, or the inner aspect of the arm or any vein in the body that will accept an IV catheter. When inserting a peripheral IV catheter, an IV infusion set is prepared, filling the IV tubing with fluid and eliminating any air, closing the fluid clamp. A tourniquet is applied proximal to the venipuncture site, and a variety of techniques are used to dilate the vein. Wearing disposable gloves, the venipuncture site is cleansed and a the vein is retracted or anchored by placing a thumb over the vein about two to three inches distal to the site. A catheter with a stylet advanced through its lumen so that the pointed tip extends beyond the cannula of the catheter or a butterfly needle is introduced into the vein by inserting the bevel into the vein at about a 20° to 30° angle with the bevel facing up in order to pierce one wall of the vein. Blood return in the tubing of the butterfly needle or the flashback chamber of the over the needle catheter indicates that the vein has been entered, and the needle is lowered towards the skin and the catheter is advanced about ¼" into the vein. The stylet is loosened and the catheter is gently advanced farther up into the vein until the hub of the catheter is against the venipuncture site. The tourniquet is loosened and the needle or stylet is removed from the catheter. The needle adaptor of the infusion tubing is secured to the hub of the catheter, and the roller clamp is opened. The flow rate may be controlled either by adjusting the roller clamp or an infusion pump, and the catheter is secured to the venipuncture site by gauze and adhesive tape.

The protective devices developed to prevent accidental needle puncture generally are designed to apply to the part of the IV infusion process. Needle shields or sheathes have been developed which are slidable, e.g., U.S. Pat. No. 5,011,475, issued Apr. 30, 1991 to Richard A. Olson (sheath slidable in slots defined in barrel of syringe); pivotal, e.g., U.S. Pat. No. 5,603,699, issued Feb. 18, 1997 to Jerry P. Shine (shield pivotally attached at base of syringe and pivotally operated by lever connected to gear mechanism); and frangible, e.g., U.S. Pat. No. 5,344,404, issued Sep. 6, 1994 to Carl L. Benson (shield in different segments secured by frangible means such as plastic shrink wrap). Some of the shields and sheathes are open over the tip of the needle, such as U.S. Pat. No. 5,267,972, issued Dec. 7, 1993 to Wayne W. Anderson (sheath spring biased to normally enclose needle, retracts around barrel of syringe when pressed against patient' skin), while others lock over and enclose the tip of the needle after use, such as U.S. Pat. No. 5,366,447, issued Nov. 22, 1994 to Carol A. Gurley (Sleeve sliding over barrel of hypodermic syringe, the sleeve having a seal at the end to seal the sleeve over the needle when fully extended) and U.S. Pat. No. 5,685,860, issued Nov. 11, 1997 to Chang, et al. (needle with a cap attached by a sleeve to the needle hub, capping needle tip after the needle is removed from the catheter hub).

Another type of protective device is disclosed in U.S. Pat. No. 5,343,875, issued Sep. 6, 1994 (clamp with troughs for the fingers to grasp an IV catheter having an injection port to protect the fingers from accidental puncture when inserting a needle through the cap). Still other devices are designed to protect against accidental dislodgement or damage to the tubing while the catheter is connected to the venipuncture site. Examples of such devices include U.S. Pat. No. 5,112,313, issued May 12, 1992 to Patricia L. Sallee (a plastic housing with an opening for the IV tubing using split grommets, the housing taped over the patient's skin over an indwelling needle) and U.S. Pat. No. 5,116,324, issued May 26, 1992 to Brierly, et al. (a base with a hinged cover, the base having tabs taped to the patient's skin and a bridge for insertion of the IV tubing between the base and the skin).

The present invention is directed towards a different problem involving the risk of spreading infection which occurs during the process of removal and disposal of a soft, flexible, indwelling peripheral IV catheter. When the IV infusion is no longer needed, the tape and dressing are removed from the venipuncture site. The IV tubing is clamped, generally by moving a roller clamp disposed between the drip chamber and the tubing to the off position. Wearing disposable gloves, the medical personnel applies a gauze sponge or alcohol pad to the venipuncture site with one hand, while grasping the hub of the catheter and withdrawing it from the venipuncture site by pulling straight back with the other hand. The medical personnel applies pressure to the venipuncture site for one to two minutes to prevent the formation of hematoma. A new dressing is taped to the venipuncture site. The used intravenous tubing with the catheter still in place is disposed of with the other sharps.

The problem which often occurs during this process is that even though the IV tubing is clamped, there is still blood and other fluids (often transparent, such as plasma, IV fluids, lymph fluids, etc.) backed up in the lumen and hub of the catheter and within the IV tubing. Very rarely is the sharps disposal container placed adjacent to the patient, and since the medical personnel often requires both hands to apply pressure to the venipuncture site as well as dressings and tape, the catheter must be released and has a tendency to spatter the fluids retained in the catheter and the end of the tubing over the patient, bed, clothing, and the floor. On a few occasions, there may be a spurt of fluid as the catheter exits the patient's skin.

Although the only wound site open at the time may be the venipuncture site, nevertheless, the fluids released from the end of the cannula may be absorbed by clothing, bed linens, floor coverings, and the like,and persist for quite some time. Since the time of Pasteur, it has been well known that microorganisms persisting in fluids are pathogenic carriers of infectious diseases. One of the more intractable and refractory challenges facing the medical profession is the persistence of nocosomial infections. Hence, it is desirable to prevent the indiscriminate splattering of blood and other fluids from the tip of the catheter upon its removal from the venipuncture site. Among other diseases which may be spread by such fluids are HIV, hepatitis, gram-positive bacteremia, staphylococcal bacteremia, and numerous other bacterial diseases.

An example of a device which partially addresses this problem is disclosed in U.S. Pat. No. 4,943,284, issued Jul. 24, 1990 to Frederick L. Ehrlich. The Ehrlich patent shows what is essentially a plastic baggie rolled up and glued around the circumference of the catheter substantially near the hub of the catheter. When the catheter is removed, the baggie is unrolled to cover the tip of the catheter and sealed with a wire tie, rubber band, adhesive, etc. There may be two such baggies, unrolling in opposite directions to cover the entire device.

There are, however, problems with the Ehrlich device. The Ehrlich device commonly requires two hands to unroll the plastic baggie, while medical personnel commonly need at least one hand available to maintain pressure on the venipuncture site and apply a dressing. It is cumbersome to use and hard to manipulate while wearing disposable gloves, particularly given the narrow diameter of the catheter hub and cannula. The plastic is prone to rupture and tear while unrolling and after sealing around the tip of the catheter. The Gurley and Chang devices are specifically adapted for use with a hypodermic syringe, in the one case depending in slots in the outside of the barrel for attaching and sliding the sheath, and in the other on a needle hub to which the cap is connected by a sleeve.

None of the above inventions and patents, taken either singularly or in combination, is seen to describe the instant invention as claimed. Thus an IV protector solving the aforementioned problems is desired.

SUMMARY OF THE INVENTION

The IV protector of the present invention is a device designed to prevent spattering of blood from the tip of a peripheral IV catheter during removal and disposal of the catheter and IV tubing. The IV protector is a flexible plastic cylinder about three inches in length and about 1.5 cm in diameter. At one end it has a projection and a mating groove clasp fastener in order to seal to seal the end of the cylinder by pinching the projection into the groove. At the other end the cylinder has internal threads adapted to lock the IV protector in a retracted position circumferentially about the IV tubing when the catheter is inserted in the venipuncture site, and adapted to lock the IV protector in an extended position circumferentially enclosing the catheter for disposal. A pair of resilient threaded washer shaped adaptors which snap fit on the IV tubing, or tubular adaptors having a hub adapted for connection to the catheter hub at one end and adapted for connection to the needle adaptor of the IV tubing at the other end are used to dispose the IV protector between the IV tubing and the catheter.

Accordingly, it is a principal object of the invention to reduce the risk of the spread of infectious diseases caused by the spattering of blood and other fluids during the removal and disposal of a peripheral IV catheter and tubing by providing a flexible plastic cylinder which extends down the IV tubing to enclose the catheter, equipped with means for sealing the end of the protector to prevent loss of fluid during disposal to a used IV infusion set.

It is another object of the invention to provide an IV protector to prevent loss of fluid from an IV infusion set during removal and disposal which may be conveniently deployed and sealed by medical personnel at the patient's bedside in order to allow medical personnel to attend to maintaining pressure on the venipuncture site and apply an appropriate dressing to the site without concern for contamination of clothing, bed linen, floor coverings, and other surroundings occasioned by loss of fluid from the used IV infusion set.

It is a further object of the invention to provide adaptors to permit the use of the IV protector with existing IV infusion sets in the form of threaded adaptors for connection to the IV tubing which threadably engage the IV protector in order to maintain the protector in a retracted position during intravenous infusion of fluids and in an extended position to enclosed the end of the catheter for disposal.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1A is an environmental, perspective view of an IV protector according to the present invention with the IV protector in a retracted position.

FIG. 2 is a perspective view of the IV protector according to the present invention.

FIG. 3 is a perspective view of a first embodiment of an adaptor for connection of the IV protector to conventional IV tubing.

FIG. 4 is a perspective view of a second embodiment of an adaptor for connection of the IV protector to conventional IV tubing.

FIG. 5 is a perspective view of a third embodiment of an adaptor for connection of the IV protector to conventional IV tubing equipped with luer lok fittings.

Similar reference characters denote corresponding features consistently throughout the attached drawings.

DETAILED DESCRIPTION OF THE PREFERRED EMBODIMENTS

Figure 1B:
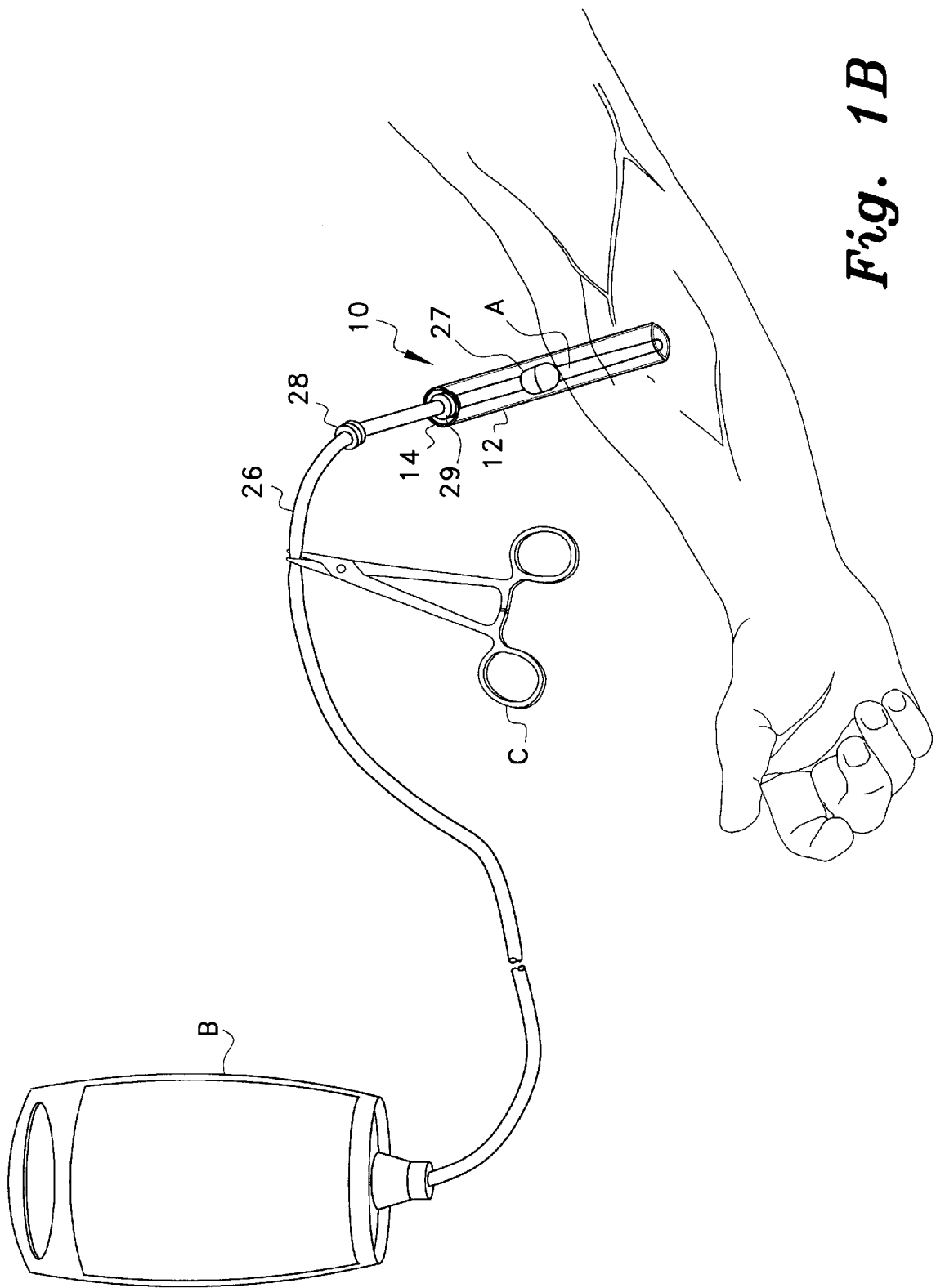
FIG. 1B is an environmental, perspective view of an IV protector according to the present invention with the IV protector in an extended position.

The present invention is an IV protector designed to reduce the risk of the spread of infectious diseases caused by the contamination of clothing, bed linens, and floor coverings occasioned by the accidental spattering of blood and other fluids associated with the removal and disposal of an intravenous infusion set and flexible catheter employed in the administration of peripheral IV therapy.

FIG. 1 shows an environmental view of the IV protector 10 of the present invention. The protector is shown more particularly in FIG. 2. The protector 10 is a flexible, plastic, hollow cylinder or tube 12 about three inches long and about 1.25 to 1.5 cm in diameter. The protector 10 is rigid enough to maintain its cylindrical shape, but flexible enough that it may be pinched closed at one end. It may be made from the same material as the IV tubing 26. The dimensions of the protector 10 are selected in order to be large enough to enclose an over the needle catheter A typically used in peripheral IV therapy. Such a catheter is normally between ¾" and 1¼" long for most applications, usually no longer than two inches at the most when applied to a deep vein.

At the end of the protector 10 proximal to the IV fluid bag, referred to for present purposes as the proximal end of the protector 10, the protector 10 has a base 14 in which an opening 16 is defined, the opening being internally threaded 18 and having a diameter slightly larger than the diameter of the IV tubing 26. At the opposite end, referred to as the distal end, the protector 10 lacks a base so that the walls of the cylinder 12 define an opening 20 with a diameter larger than the diameter of the IV tubing 26. On the interior of the walls of the cylinder 12 adjacent the opening 20 are a projection 22 and matching groove 24 clasp fastener adapted to seal the distal end of the protector 10 upon pinching the distal end to close the opening 20, similar to a Ziploc® clasp fastener. The seal is such that with the opening 20 pinched closed, fluids are prevented from exiting the distal end of the protector.

FIG. 1A shows the protector 10 disposed between the IV fluid bag B and the catheter A. The dressing has been removed from the venipuncture site preparatory to removing the catheter A.

Figure 1C:
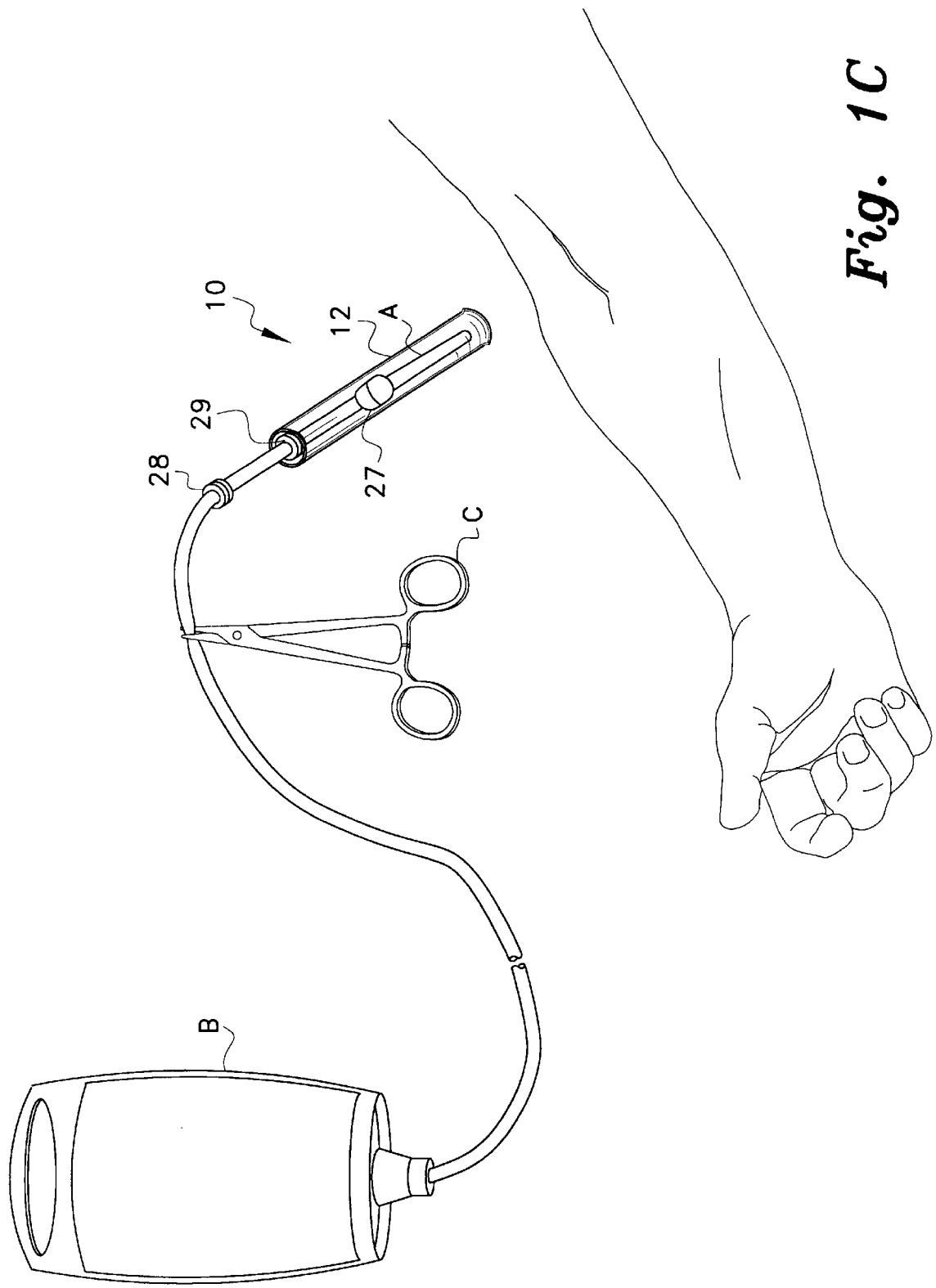
FIG. 1C is an environmental,perspective view of an IV protector according to the present invention with the catheter removed from the venipuncture site and the end of the protector sealed for disposal of the unit.

As shown in FIG. 1A, the protector 10 has a retracted position in which the protector 10 is retained circumferentially disposed around the IV tubing 26 when the catheter A is inserted in the venipuncture site. The protector 10 is maintained in the retracted position by means of a threaded connector 28 disposed annularly about the circumference of the IV tubing 26, as shown more clearly in FIG. 1B with the protector 10 in the extended position. For purposes of illustration, the IV tubing is shown clamped by a hemostat C, although in practice the tubing 26 would probably be clamped simply by rotating the wheel of a roller clamp (not shown) disposed between the drip chamber and the IV tubing 26 to the off position. The internal threads 18 defined in the base 14 of the protector 10 engage the threaded connector 28 in such a manner that a clockwise twist of the cylinder 12 onto the threaded connection 28 is sufficient to lock the protector 10 in a retracted position, while a counter clockwise twist releases the protector 10 to lower into an extended position encircling the catheter A, the opening 16 in the base 14 being of sufficiently large diameter that the protector 10 is slidable on the IV tubing 26. The intravenous tubing 26 is provided with a second threaded connector 29 such that a counterclockwise twist locks the protector 10 in an extended position. Once extended, the protector 10 may be pinched closed at its distal end in order to seal off the open tip end of the catheter A as shown in FIG. 1C.

In use, the protector 10 is locked in the retracted position by a clockwise twist securing the protector to threaded connector 28 while the catheter is inserted in the venipuncture site. The threaded connector 28 maintains the protector 10 in a position where it does not interfere with the venipuncture site and prevents the protector 10 from moving on the tubing 26. When the catheter A is to be removed, the tubing 26 is clamped, the dressings are removed from the venipuncture site, a gauze sponge is placed over the venipuncture site, and the catheter A is pulled out of the vein. A counterclockwise twist releases the protector 10 from threaded connector 28 so that the protector 10 may be moved to the extended position, and approximated to the skin as shown in FIG. 1B to prevent spurting of blood and other fluids, if desired. A counterclockwise twist locks the protector on threaded connector 29, locking the protector in the extended position. The distal end of the cylinder 12 is pinched, sealing the end of the cylinder 12 as the projection 22 snaps into the groove 24. The tubing 26 and catheter A can then be set aside while the medical personnel applies pressure to the venipuncture site for one to two minutes, and applies a dressing and tape to the site. The IV tubing 26 and catheter A may then be disposed of as a unit in a container designated for sharps.

Preferably, the threaded connectors 28 and 29 are made integrally with the IV tubing 26. However, the protector 10 can be used with existing conventional IV tubing 26 by the use of adaptors. A first embodiment of such an adaptor 30 is shown in FIG. 3. In this form the adaptor 30 is simply an annular ring with threads on its exterior surface. The adaptor 30 is made of a flexible, elastic material so that it may be stretched to fit over the IV tubing 26 and adjusted to the required height, snapping into place axially on the tubing. Two such adaptors 30 are required, one with clockwise threads to retain the protector 10 in a retracted position, and the other with counterclockwise threads to lock the protector 10 in an extended position.

A basic version of a second embodiment of an adaptor 32 is shown in FIG. 4. The second adaptor 32 is a short length of IV tubing 34 having a first hub 36 and a second hub 38 at either end of the tube 34. Normally the IV tubing 26 has a needle adaptor 27 for connection to a butterfly needle or an over-the-needle catheter A. Various forms of connectors are used, such as a slip-lock, luer lok, etc. The first hub 36 is adapted to receive the needle adaptor 27 at the end of the IV tubing 26. The second hub 38 is adapted for connection to the catheter A. The adaptor 32 has a threaded connector 40 at or near the first hub 36 to lock the protector 10 in a retracted position, and a second threaded connector 42 at or near the second hub 38 for locking the protector 10 in an extended position.

A practical environmental view of an adaptor according to the second embodiment is shown in FIG. 5. FIG. 5 shows such an adaptor 44 with a catheter A connected at one end and IV tubing 26 connected at the other end. The adaptor 44 is connected to the catheter A by a luer lok connector 46, and the IV tubing 26 is also connected to the hub 50 of the adaptor 44 by a luer lok connector 48. A luer lok connector is essentially a form of connector with tabs at one end which thread into a received at the other end, so that, for example, a needle may be locked onto a syringe by inserting the needle hub into a luer lok fitting and twisting to secure the needle to the syringe. The adaptor 44 has a length of tubing 52 between the hub 50 connected to the IV tubing 26 and the luer lok 46 connected to the catheter A. Disposed annularly about the tube 52 are a first threaded connector 54, shown holding the protector 10 in a retracted position, and a second threaded connector 56, adapted for locking the protector 10 in an extended position. Hence, the IV tubing 26 is connected to the adaptor 44 at one end in the same manner that it would ordinarily be connected to the catheter A, and the catheter A is connected to the other end of the adaptor 44 in the same manner it would ordinarily be connected to the IV tubing 26.

It is to be understood that the present invention is not limited to the embodiments described above, but encompasses any and all embodiments within the scope of the following claims. It will be understood that for purposes of illustration the threaded connectors 28, 29, 54 and 56 have been shown projecting from the tubing 26 as an annular disk. In practice the threads are closely aligned with the tubing 26 so that ordinarily no form of guide should be required to maintain the threaded opening 16 defined in the base 14 of the protector 10 axially aligned with the threaded connectors 28 and 29 or 54 and 56; however it is well known in the art to add such guides if required.

We claim:

1. An IV protector for sealing off the end of a catheter used in peripheral intravenous infusion therapy in order to prevent loss of fluid from the catheter and IV tubing connected to an IV fluid bag, the IV tubing having a needle adaptor at one end of the tubing, upon removal and disposal from a venipuncture site, comprising a plastic cylinder, the cylinder being flexible and hollow and having a proximal end and a distal end, the proximal end being proximal to the IV fluid bag and the distal end being distal to the IV fluid bag, the cylinder having:

a) a base at the proximal end of said cylinder, the base having an opening defined therein and locking means for locking said protector axially about the IV tubing in a retracted position, whereby said protector is disposed in a retracted position about the IV tubing while the catheter is inserted in the venipuncture site, and for locking said protector axially about the IV tubing in an extended position whereby said protector is disposed about the catheter after removing the catheter from the venipuncture site, wherein said locking means comprises internal threads defined in the base of said cylinder, said threads being adapted for engaging a threadable connector disposed about the IV tubing; and b) a projection and matching groove clasp fastener at the distal end of said cylinder for sealing the end of the cylinder in order that said protector encloses the catheter and is sealed around the tip end of the catheter to prevent loss of fluid from the catheter and the IV tubing.

2. The IV protector according to claim 1, further comprising an adaptor, said adaptor comprising a length of adaptor tubing having a first hub at one end of the adaptor tubing and having a second hub at the other end of said adaptor tubing, the first hub being adapted for connection to the needle adaptor of the IV tubing, the second hub being adapted for connection to the catheter, said adaptor further including a first threaded connector at said first hub adapted for locking said protector in the retracted position, and a second threaded connector at said second hub adapted for locking said protector in the extended position.

3. The IV protector according to claim 2, wherein said first hub is adapted for connection to a luer lok fitting on the needle adaptor of said IV tubing and wherein said second hub has a luer lok fitting adapted for connection to the catheter.

4. The IV protector according to claim 1, further comprising IV infusion tubing having an integral first threaded connector and an integral second threaded connector, said threaded connectors being axially disposed about the circumference of the IV infusion tubing at the end of the tubing distal from its connection to said IV fluid bag, said first threaded connector being adapted for engaging said locking means in order to lock said protector in the retracted position, and said second threaded connector being adapted for locking said protector in the extended position.

5. The IV protector according to claim 1, further comprising a first adaptor and a second adaptor, said first adaptor and said second adaptor each comprising an annular ring, the annular ring being flexible and elastic and adapted for snap fitting axially around the IV tubing of a conventional IV infusion set, said first adaptor being adapted for threadably engaging the locking means of said protector in order to lock said protector in the retracted position, and said second protector being adapted for threadably engaging the locking means of said protector in order to lock said protector in the extended position.

* * * * *